United States Patent [19]

Weissman

[11] Patent Number: 4,850,874
[45] Date of Patent: Jul. 25, 1989

[54] DENTAL PIN SYSTEM

[75] Inventor: Bernard Weissman, New York, N.Y.

[73] Assignee: IPCO Corporation, White Plains, N.Y.

[21] Appl. No.: 3,065

[22] Filed: Jan. 14, 1987

[51] Int. Cl.$^4$ .............................................. A61C 5/04
[52] U.S. Cl. ................................................... 433/225
[58] Field of Search ......................................... 433/225

[56] References Cited

U.S. PATENT DOCUMENTS

| | | | |
|---|---|---|---|
| 3,675,328 | 7/1972 | Weissman | 433/225 |
| 3,874,081 | 4/1975 | Franklin et al. | 433/225 |
| 3,928,915 | 12/1975 | Ellman | 433/225 |
| 4,187,611 | 2/1980 | Chan | 433/225 |
| 4,189,834 | 2/1980 | Smith | 433/225 |
| 4,397,395 | 8/1983 | McKelvey | 433/79 |

Primary Examiner—Gene Mancene
Assistant Examiner—Adriene J. Lepiane
Attorney, Agent, or Firm—Helfgott & Karas

[57] ABSTRACT

A dental pin system including an enlongated pin having a plurality of pin sections each of which can be sheared from the next adjacent section by means of a reduced diameter frangible throat portion. The upper end of the pin includes a flattened tang which is securely inserted within an adaptor member. The adaptor member is barrel-shaped with an opposing pair of knobs, diametrically projecting from the midsection of the barrel. The adaptor member can be removably inserted into a pair of receiving slots at the end of a shank. The upper end of the shank is adapted for direct driving by means of a handpiece or hand driver. A plurality of the adaptor members, each color coded to identify their respective pin, can all be mounted on a plate in a prepackaged kit and a single shank can be used to connect to each adaptor member in turn whereby the shank is reused for the adaptors.

21 Claims, 5 Drawing Sheets

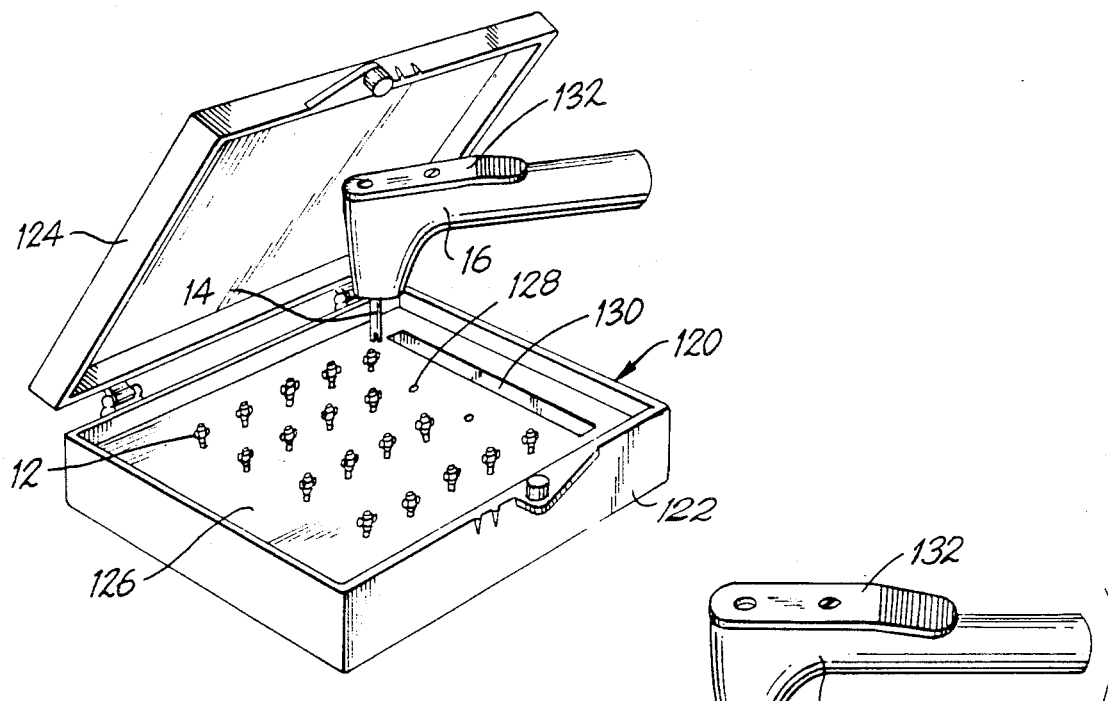
FIG. 1
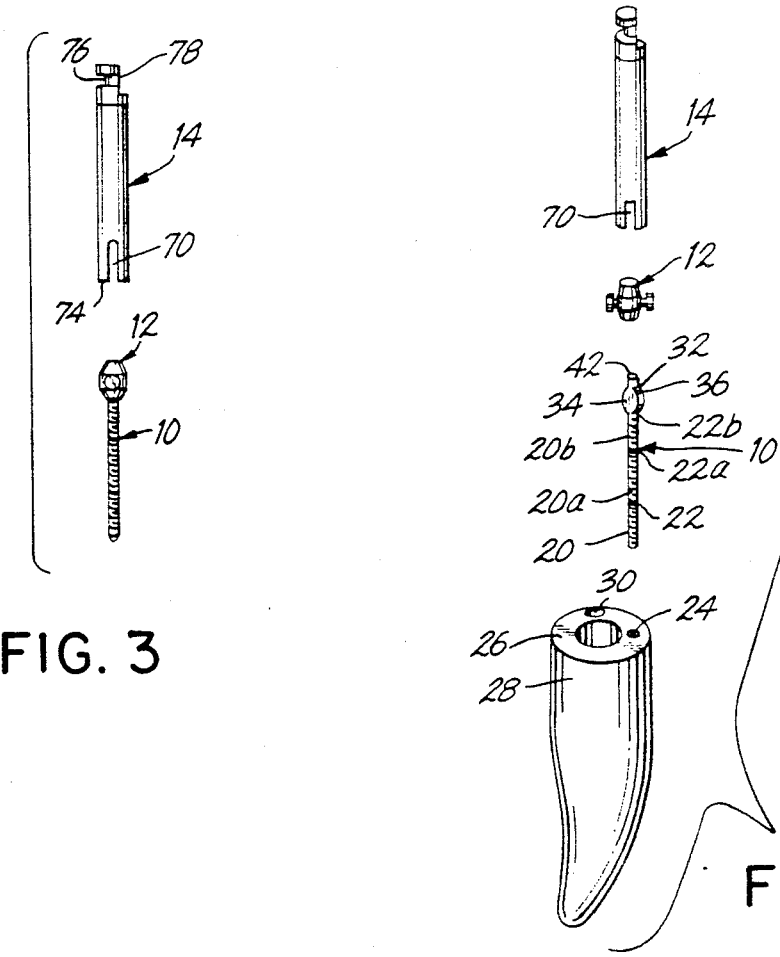
FIG. 3
FIG. 2

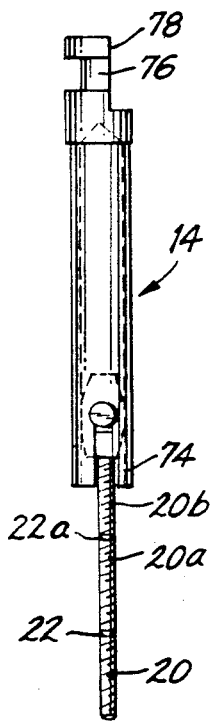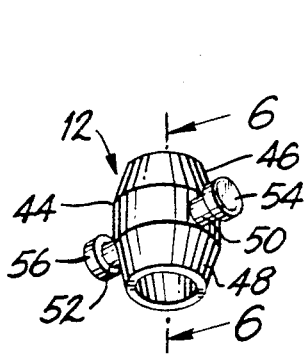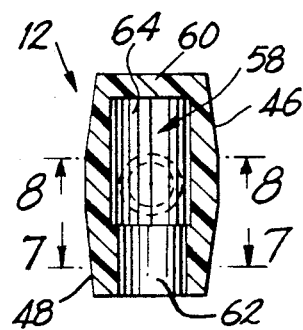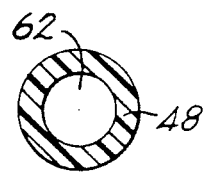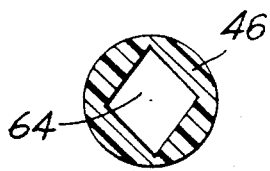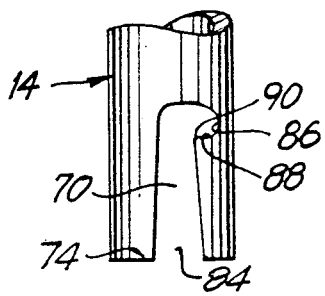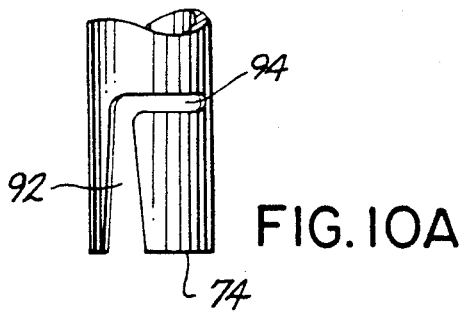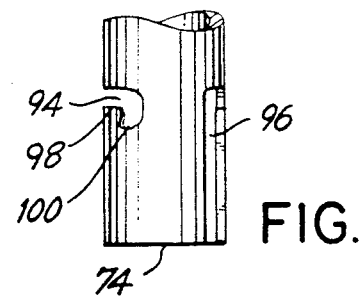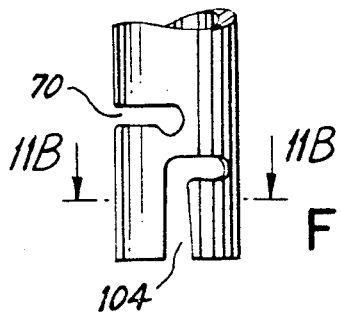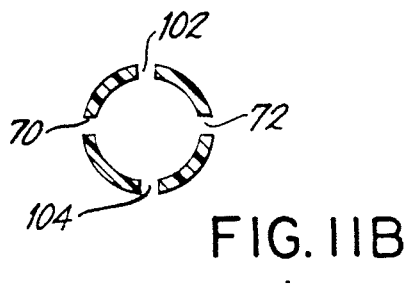

DENTAL PIN SYSTEM

BACKGROUND OF THE INVENTION

This invention relates to dental apparatus, and more particularly, to a dental pin system, including dental pins secured in a mounting adaptor, which can be received within a shank whose other end is operatively connected to a handpiece or manual driver.

Dental pins are utilized in dental procedures for securing a superstructure upon a tooth stub. The tooth stub may be initially prepared with a number of apertures. The dental pins are threaded into the apertures with a portion of the dental pins projecting above the tooth stub. The superstructure is then built onto the tooth stub with the upper portions of the dental pins being used to retain the superstructure placed onto the tooth stub.

One type of dental pin that has been utilized has a plurality of sections, each functionally serving as a separate dental pin. The sections are separated by reduced diameter frangible throats serving as shear points. One such dental pin is described in U.S. Pat. No. 3,675,328, assigned to the assignees of the present invention. In that patent, the plurality of dental pin sections have an enlarged head portion at their upper end, which head portion is directly inserted into the lower end of a shank. The upper end of the shank is available for insertion into a driving member, such as a handpiece or manual driver. Such system has been available as the TMS Thread Mate System.

An improvement in the multiple section pin is described in U.S. Pat. No. 4,202,101. In such patent, the upper end or head portion of the multiple sectioned pin includes an outer peripheral edge, which is arcuately shaped. Upon insertion of the pin in the shank, the pin can sway or pivot within the shank and thereby aid in the insertion of the pin in the aperture in the tooth stub. This pin system is available as the Link series pins.

In the various pin systems, it is typical to have the pin securely inserted within the shank portion whereby the pin and shank portion is available as a single unit device. To some extent this is convenient, since the shank is loaded directly into the handpiece and already includes a pin projecting from the end of the shank. However, it also means that the shanks must be continuously thrown away after the use of each pin, and the shanks are therefore not reusable.

SUMMARY OF THE INVENTION

Accordingly, the present invention provides for a dental pin having a plurality of individual dental sections which sections are separated from each other by reduced diameter throat portions. This permits shearing of each dental section, from the next section. Such pin is typical of the Link pin. However, the present invention calls for a mounting adaptor, in which the head of the pin is inserted. The mounting adaptor is removably inserted into the end of a shank portion through a twist lock arrangement.

A kit can be provided having a plurality of pins with their mounting adaptors secured onto their heads and the pins within their mounting adaptors projecting from a base plate in the kit. A single shank can be provided for use with the plurality of pins and mounting adaptors. All of this can be contained into a single package. The single shank can then be utilized to successively grasp and lock onto each of the mounting adaptors. The multiple sectioned pin depending from the mounting adaptor is then utilized to fill a series of apertures in a tooth stub. The mounting adaptor is then removed from the shank and the shank can then be re-used to grasp and lock onto the next mounting adaptor with its depending pin.

Each of the mounting adaptors can be formed in a different color, with the color representing the size of the pin projecting therefrom. Each kit could contain either a series of mounting adaptors of the same color size, or the kit could contain different rows with each row being a different color and, accordingly, a different size pin. Other arrangements could also be made.

Through the use of this invention, a single shank can be re-used for a number of different pins, with each pin being connected to the end of the shank by its own mounting adaptor. The pins and mounting adaptors can be pre-assembled, and the dentist or technician connects the mounting adaptor to the shank portion.

Alternately, the shank could be built into a handpiece and permanently secured as part of the handpiece. The handpiece itself, with the shank projecting therefrom, is then used to grasp and lock onto the various mounting adaptors which project from the base surface of the kit package.

It is therefore an object of the present invention to provide a dental pin system having dental pins mounted into mounting adaptors, with the mounting adaptors being able to be removably secured into the distal end of a shank.

Another object of the present invention is to provide a dental pin system having dental pins of multiple sections, which can be sheared from each other with the dental pin having a single enlarged head inserted into a mounting adaptor.

Another object of the present invention is to provide a dental system having a dental pin secured into a mounting adaptor, and a shank which can be used to grasp and removably lock onto the mounting adaptor with the shank available for insertion into a handpiece or hand driver.

Still another object of the present invention is to provide a dental pin kit having a plurality of dental pins with their enlarged heads inserted into a respective mounting adaptor, all of the mounting adaptors projecting from the base plate of a kit package and a single shank being usable for selectively grasping and locking onto the mounting adaptors.

A further object of the present invention is to provide a plurality of dental pins, each respectively secured within a mounting adaptor with the mounting adaptors being color coded to identify the size of the pin projecting therefrom.

The aforementioned objects, features and advantages of the invention will, in part, be pointed out with particularity, and will, in part, become obvious from the following more detailed description of the invention, taken in conjunction with the accompanying drawing, which forms an integral part thereof.

BRIEF DESCRIPTION OF THE DRAWING

In the drawing:

FIG. 1 is a perspective view showing a kit having a series of pins, each depending from a mounting adaptor and the mounting adaptors projecting from the base of the kit and available for selective attachment to a shank depending from a handpiece;

FIG. 2 is an exploded view showing the parts of the system for insertion into an aperture in a tooth stub;

FIG. 3 is an exploded view showing the pin secured within the mounting adaptor and the adaptor available for removable insertion into the distal end of the shank;

FIG. 4 is a side elevational view showing the pin and mounting adaptor projecting from the end of the shank;

FIG. 5 is a perspective view of the mounting adaptor;

FIG. 6 is a cross-sectional view taken along lines 6—6 of FIG. 5;

FIG. 7 is a cross-sectional view taken along lines 7—7 of FIG. 6;

FIG. 8 is a cross-sectional view taken along lines 8—8 of FIG. 6;

FIG. 9 shows one embodiment of the slot in the end of the shank;

FIGS. 10a and 10b show another embodiment of slots at the end of the shank;

FIGS. 11a and 11b show, respectively, a side and end view of the use of two pairs of different sized slots at the end of a shank portion;

In the various figures of the drawing, like reference characters designate like parts.

DESCRIPTION OF THE PREFERRED EMBODIMENT

Figures 12, 13, 14:
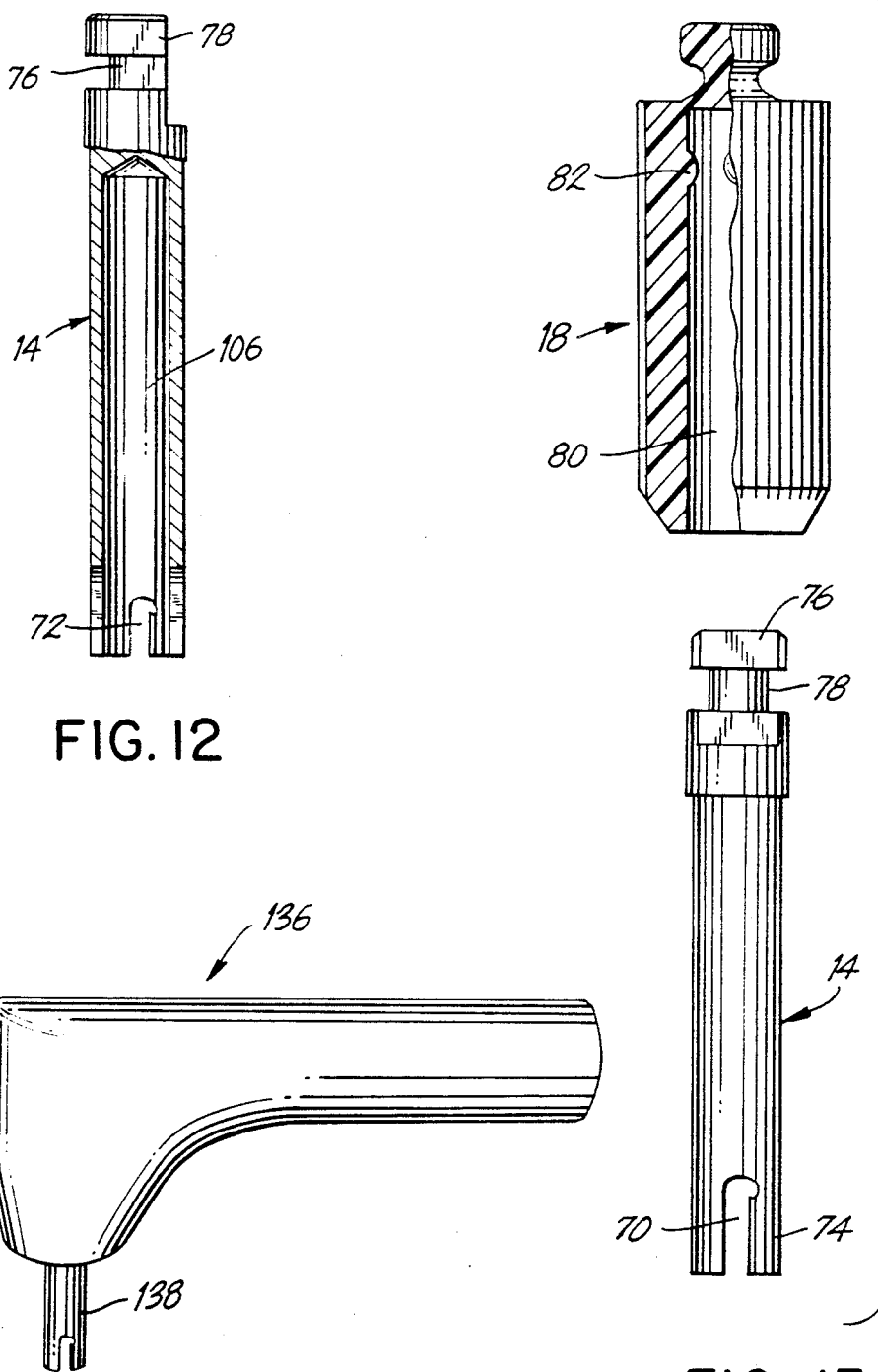
FIG. 12 is a cross-sectional elevational view through the shank portion with a part of the shank portion broken away.
FIG. 13 is an exploded view showing insertion of the shank into a manual hand tool.
FIG. 14 shows a handpiece with a permanently mounted shank, which can be utilized with the present invention.

Referring now to FIG. 2, the dental pin system of the present invention includes an elongated dental pin, shown generally at 10, which is securely mounted within a mounting adaptor 12. The mounting adaptor can be removably assembled into the distal end of a shank 14. The upper end of the shank can then be inserted into a handpiece 16 as shown in FIG. 2. Alternately, as shown in FIG. 13, the shank 14 can be mounted within a manual hand driver 18.

The dental pin can best be seen in various figures of the drawing, including FIGS. 2, 3, 4 and 15, and is of a type typically described in the aforementioned U.S. Pat. No. 4,202,101. Specifically, the pin comprises a plurality of individual in sections, 20, 20a, 20b. Each of the pin sections is separated by a reduced diameter throat section 22, 22a, 22b. The reduced diameter throat section can be sheared as each of the pin sections beneath the throat section has been inserted in the aperture in the tooth stub.

Specifically, the lowermost section 20 would first be threaded into an aperture 24 provided into a surface 26 of a tooth stub 28. The pin would be threaded into the aperture until it reaches the bottom of the aperture, at which time it will shear at the throat 22, thereby severing the lower pin section 20 from the remaining sections. The aperture in sized so that a lower part of the pin section 20 is received within the aperture with at least a portion of the pin section projecting above the aperture and upon which a superstructure can be built.

The next section 20a would then be threaded into another aperture 30, also provided in the tooth stub, whereby a number of the pin sections could be sequentially threaded into various apertures in the tooth stub, one right after the other.

In order to be sure that the lowermost section 20 severs before the next section, the throats 22, 22a, and 22b are of successively larger diameter size. In this manner, the throat 22 will shear before the throat 22a.

Figure 15:
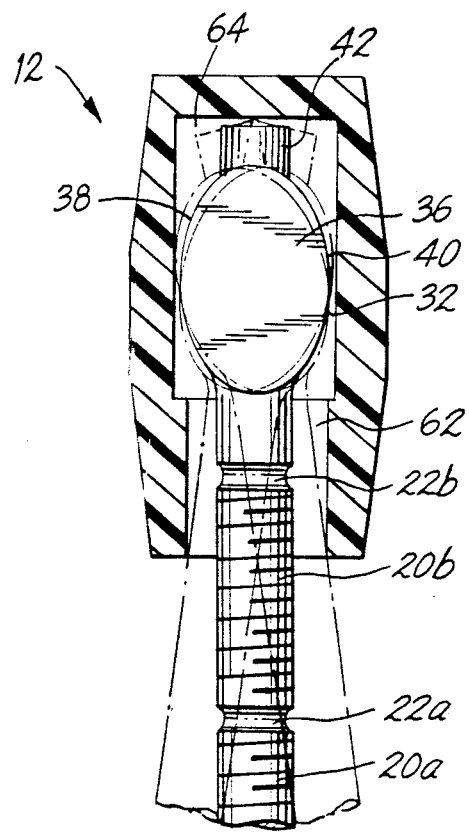
FIG. 15 is a cross-sectional view showing the assembly of the pin in the mounting adaptor and showing the availability of the pin swaying within the mounting adaptor.

The upper end of the elongated pin includes an enlarged head portion 32 formed as a flattened tang having front and rear surfaces 34, 36. The outer peripheral edges are curved to form the outer arcuate edges 38, 40 as best seen in FIG. 15. An upper stem 42 terminates the upper end.

The mounting adaptor 12 can best be seen in FIGS. 5-8 as being formed as a cylindrical barrel configuration having a central cylindrical section 44 with the upper end 46 being tapered into a frustoconical shape, and, likewise, the lower end 48 tapered to form a frustoconical portion.

Diametrically projecting from the mid-section 44 are a pair of opposing stems 50, 52, each of which terminates in a respectively enlarged knob 54, 56. Internally, there is provided a hollow chamber 58, which extends almost entirely through the mounting adaptor 12, but terminates short of the upper end, providing a roof portion 60 above the chamber. The lower portion of the chamber 62 is of circular cross-section, while the upper chamber 64 is diamond shaped in cross-section, as shown in FIGS. 7 and 8.

As shown in FIGS. 3 and 15, the upper end of the pin, including the enlarged head, enters into the lower circular shaped portion of the chamber 62 and then continues upwardly in the chamber until it is received within the diamond-shaped cross-sectional part 64. It is then secured in place so that it cannot fall out of the mounting adaptor. In fact, such assembly of the elongated pin 10 into the mounting adaptor 12 occurs by the manufacturer and is preassembled prior to distribution. As shown in FIG. 15, the upper end of the dental pin can sway within the chamber in the mounting adaptor 12. Such sway or pivot is one of the benefits of the Link series pin system as has heretofore been explained in the aforementioned U.S. Pat. No. 4,202,101.

At the lower end of the shank 14, there are provided a pair of diametrically opposed slots 70, 72. The slots start at the lower distal end 74 of the shank and extend part way up along the longitudinal shank. At the upper end of the shank, there is provided a coupling arrangement for connecting the shank to a handpiece or a hand driver. Specifically, there is provided a reduced diameter neck portion 76 and a flattened side portion 78. Such coupling arrangement has been heretofore described in connection with U.S. Pat. No. 4,202,101.

In addition to being insertable within a handpiece, such coupling arrangement facilitates entry into the hand driver, as shown in FIG. 13. The hand driver would include an internal chamber 80 with inwardly directed ribs 82 at its upper end. Such coupling arrangement has been described in the aforementioned U.S. Pat. No. which is herein incorporated by reference.

One form of the slot is shown in FIG. 9 and includes a mouth portion 84 which tapers upwardly, terminating in a horizontal section 86. The horizontal section includes a lower dipped portion 88 and a constricted neck portion 90. In assembly, the opposing stems 50, 52 would be slid into the opposing slots 70, 72 until they reached the constriction. It would then be required to force twist the adaptor so that it passes the constriction, after which it will be securely received within the lower dipped portions 88. Such twist lock arrangement secures the mounting adaptor in place at the distal end of the shank portion, as best shown in FIG. 4.

An alternate arrangement of the slots is shown in FIGS. 10a and 10b. Again, the slots begin at the lower end 74 and extend upwardly along an upwardly tapered section 92. The horizontal section 94, however, extends for a considerable distance, by way of example, at least a quarter turn around the end of the shank portion. The next opposing slot 96 would be 180 degrees away from the first slot 92 and would, likewise, have a horizontal section, which would extend approximately a quarter of the shank portion. With this arrangement, the knobs are locked in place and positioned at a location of strength of the shank portion, where there is considerable amount of material beneath the horizontal slot portion at the point of attachment. Again, even with the slots 94, there is provided a narrow constriction 98 before the lower dipped portion 100 to receive the stems locked in place.

As shown in FIGS. 11a and 11b, in addition to the first pair of opposing slots 70, 72 a second opposing pair 102, 104 can also be included. However, the second opposing pair would extend only part way along the height of the first opposing pair of slots 70, 72. With this arrangement, the mounting adaptor can be inserted in either of the two opposing pairs to obtain a high and low connecting position for the mounting adaptor, depending upon the length of the pin. For long pins, the mounting adaptor would be inserted within the pair of opposing slots 70, 72, thereby putting the mounting adaptor at an interior portion of the shank. For shorter pins, the other pair of slots 104, 102 would be utilized, whereby the mounting adaptor would not be inserted as far within the shank and the pin could project adequately from the shank portion. As shown in FIG. 12, the interior of the shank would include a hollow chamber 106 to receive the adaptor therein.

Figure 16:
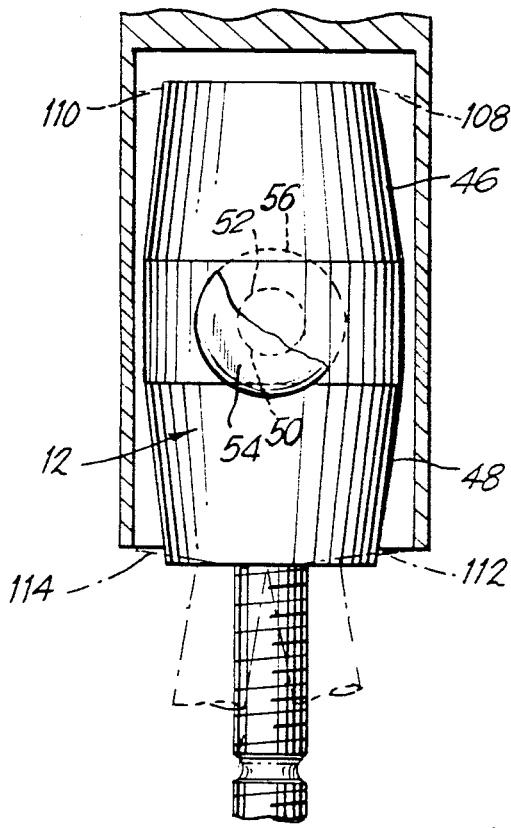
FIG. 16 shows a cross-sectional view of the mounting adaptor assembled in the end of the shank and showing the ability of the mounting adaptor swaying within the distal end of the shank.

With the adaptor in place, as shown in FIG. 16, in addition to the sway of the pin within the adaptor, there is also provided sway of the adaptor within the shank portion. The frustoconical shape 46 at the upper end of the adaptor and at 48 at the lower end of the adaptor permits the sway portions as shown in the dotted lines 108,110 at the upper end and 112, 114 at the lower end. Such sway or pivot is one of the features of the Link arrangement, as was heretofore described in the above-mentioned patent.

As shown in FIG. 1, since each pin is inserted within its own mounting adaptor, it is possible to provide a kit arrangement having a package 120 with a base portion 122 and a hinged cover portion 124. A support plate 126 is provided in the base portion 122 with a plurality of holes 128. Projecting from each of the holes is one of the assembled mounting pins in it respective mounting adaptor. The mounting adaptors would project above the support plate 126. Each of the mounting adaptors, or at least the projecting knobs thereof, could be color coded according to the size of the pin. Thus, just by looking at the mounting adaptors which stick up from the support plate, the user can know the size of the pin.

A single shank 14 can be utilized. The shank could be stored within a channel 130 provided in the plate 126. The shank could then be inserted into the handpiece 16 and locked in place by means of the locking arrangement 132. With the shank mounted in the handpiece, the handpiece can be lowered onto the mounting adaptor and can grasp one of the mounting adaptors in the appropriate slots. The mounting adaptor with the pin projecting therefrom is then twist locked into the slots in the shank portion and the assembly is ready for placement of the pins in the apertures of the tooth stub.

After all of the pins have been sheared and appropriately inserted into respective apertures in the tooth stub, the mounting adaptor, with the remaining head portion imbedded therein can be twisted out of the shank portion and discarded. The shank portion can then be re-used to pick up another pin and mounting adaptor assembly from the kit.

In this manner, the shank can be continuously reused for a plurality of projecting pins and mounting adaptors. Since the shank portion can be re-used, it can actually be formed as a permanent attachment to the handpiece, as shown in FIG. 14. Specifically, the head 134 of the handpiece 136 includes permanently mounted shank 138. As a result, the shank does not have to be continuously remounted into the handpiece, but the whole handpiece, with the shank, can be sold as a single unit and utilized for all of the pins with their respective mounting adaptors, as shown in FIG. 1.

Figure 17:
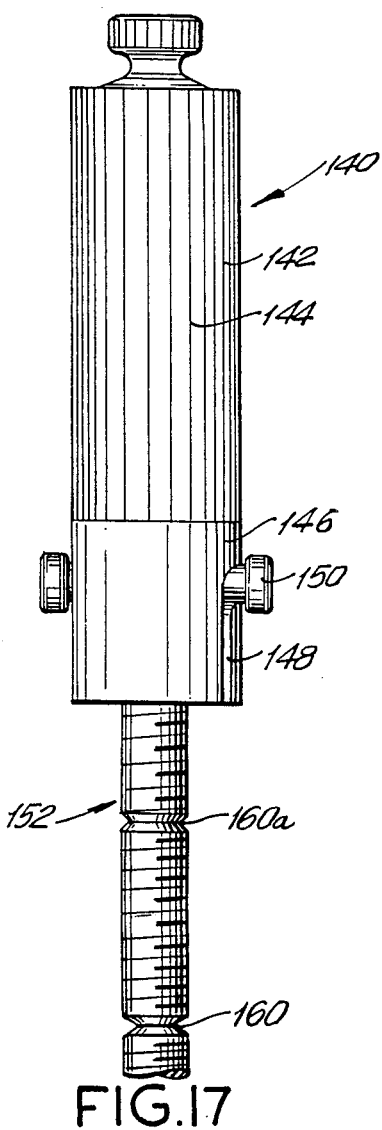
FIG. 17 shows an elevational view of the mounting adaptor assembled in the end of a combination hand driver and shank unit.

As shown in FIG. 17, the shank can be formed as an integral unit with a handpiece 140. The upper portion 142 includes serrations 144 to permit an easier grasp. The lower portion 146 includes the slots 148 for receiving the mounting adaptor 150 with the pin 152 projecting therefrom. The tool can be reused with other adaptors.

FIG. 17 also shows the progressively increasing diameter 160, 160a of the reduced diameter sections of the pin 152 as the sections progress toward the head portion of the pin.

There has been described heretofore the best embodiment of the invention presently contemplated. However, it is to be understood that various changes and modifications may be made thereto, without departing from the spirit of the invention.

What is claimed is:

1. A dental pin system comprising a dental pin having a threaded portion at one end for insertion into an aperture provided in a tooth stub with a portion of the pin projecting above the surface of the tooth stub for retention of a superstructure onto the tooth stub, and a head portion at an opposite end of the pin, a mounting adaptor having an internal bore for receiving said head portion therein to securely retain a dental pin projecting from the adaptor, and coupling means on the adaptor for removable connection to one end of a shank, whose other end has an arrangement for driving the shank, wherein said coupling means comprises a pair of laterally projecting knobs for insertion into slots extending into the lower end of a shank.

2. A dental pin system as in claim 1, wherein said knobs comprise a stem portion extending from the barrel, and an enlarged head facilitating insertion and removal from the slots.

3. A dental pin systems as in claim 2, wherein said enlarged heads are color coded to identify the size of the pin.

4. A dental pin system comprising a dental pin having a threaded portion at one end for insertion into an aperture provided in a tooth stub with a portion of the pin projecting above the surface of the tooth stub for retention of a superstructure onto the tooth stub, and a head portion at an opposite end of the pin, a mounting adaptor having an internal bore for receiving said head portion therein to securely retain a dental pin projecting from the adaptor, and coupling means on the adaptor for removable connection to one end of a shank, whose other end has an arrangement for driving the shank, wherein said threaded portion comprises a series of individual threaded sections, such sections being separated by reduced diameter portions providing shear points for separating each section of the pin upon its respective insertion into an aperture in a tooth stub, and wherein the reduced diameter portions have progressively increasing diameters as the sections progress toward the head portion of the pin, whereby remote sections will shear before medial sections.

5. A dental pin system as in claim 4, wherein said internal bore extends longitudinally at least part way through said adaptor.

6. A dental pin system as in claim 4, wherein said head portion is a flat tang and at least a portion of said interior bore has a cross-sectional configuration to matingly receive said flat tang.

7. A dental pin system as in claim 6, wherein the lateral peripheral edges of said flat tang are arcuately bowed.

8. A dental pin system as in claim 4, wherein said internal bore has a forward section with a circular crossectional configuration.

9. A dental pin kit comprising a plurality of dental pins for insertion into a tooth for retaining a superstructure on the tooth, each dental pin being secured within and depending from a respective adaptor member, and at least one shank member having one end for removably coupling onto the adaptor member and the other end for rotatingly driving the shank to thereby thread the pins into the tooth, wherein said adaptor member comprises a pair of laterally projecting knobs and said shank member has a pair of diametrically opposed longitudinal slots extending from its distal end for receiving the knobs. head portion therein to securely retain a dental pin projecting from the adaptor, and coupling means on the adaptor for removable connection to one end of a shank, whose other end has an arrangement for driving the shank, wherein said threaded portion comprises a series of individual threaded sections, such sections being separated by reduced diameter portions providing shear points for separating each section of the pin upon its respective insertion into an aperture in a tooth stub, and wherein the reduced diameter portions have progressively increasing diameters as the sections progress toward the head portion of the pin, whereby remote sections will shear before medial sections.

10. A dental pin kit as in claim 9 wherein said knobs comprise a stem portion for sliding along said slots, and an enlarged head extending outside said slots for facilitating insertion and removal of the adaptor member from the shank.

11. A dental pin kit as in claim 10, wherein said knobs are color coded to identify the size of the pin in the adaptor.

12. A dental pin kit as in claim 9, wherein said slots are inverted L-shaped slots for twist locking of the knobs in place.

13. A dental pin kit as in claim 12, wherein the horizontal leg of the slot has a restricted mouth portion requiring for twisting of the knob in place.

14. A dental pin kit as in claim 9, and further comprising a second pair of diametrically opposed longitudinal slots circumferentially oriented with respect to the first pair of slots, one of said pair of slots extending a greater longitudinal length along the shank portion than the other pair of longitudinal slots.

15. A dental pin kit as in claim 9, wherein said shank portion has a central bore and said adaptor member is substantially cylindrical for insertion into the central bore.

16. A dental pin kit as in claim 15, wherein the upper and lower ends of the adaptor are frustoconically shaped.

17. A dental pin kit as in claim 9, wherein the other end of the shank has a reduced diameter neck portion and a vertical wall forming a lock for removable insertion into a dental handpiece.

18. A dental pin kit as in claim 9, wherein the other end of the shank is adapted for removable insertion into a manual hand driver.

19. A dental pin kit as in claim 9, wherein the other end of the shank is permanently mounted in a dental handpiece.

20. A dental pin kit as in claim 9, and further comprising a case, storage means in said case for retaining said pins in said case, and wherein the adaptor members sit above the storage means for access by the shank member.

21. A dental pin kit as in claim 9, wherein the other end of the shank includes gripping means whereby said shank can be used as a hand driver.

* * * * *